United States Patent [19]

Szantay et al.

[11] 4,052,404

[45] Oct. 4, 1977

[54] INDOLO (2,3-α)QUINOLIZINES

[75] Inventors: Csaba Szantay; Lajos Szabo; Gyorgy Kalaus; Egon Karpati; Laszlo Szporny, all of Budapest, Hungary

[73] Assignee: Richter Gedeon Vegyeszeti Gyar Rt., Budapest, Hungary

[21] Appl. No.: 635,092

[22] Filed: Nov. 25, 1975

[30] Foreign Application Priority Data

Nov. 26, 1974 Hungary .................. RI-555

[51] Int. Cl.² .......................... C07D 455/02
[52] U.S. Cl. .................... 260/293.53; 260/294.9; 424/267
[58] Field of Search .................. 260/293.53

[56] References Cited

U.S. PATENT DOCUMENTS

| 3,454,583 | 7/1969 | Kuehne | 260/294.3 |
| 3,536,725 | 10/1970 | Schut | 260/294.9 |
| 3,755,333 | 8/1973 | Szantay et al. | 260/293.53 |
| 3,937,709 | 2/1976 | Sevenet et al. | 260/293.53 |
| 3,884,927 | 5/1975 | Martel et al. | 260/293.53 |
| 3,962,258 | 6/1976 | Archibald et al. | 260/293.53 |

Primary Examiner—Natalie Trousof

Attorney, Agent, or Firm—Toren, McGeady and Stanger

[57] ABSTRACT

The invention relates to new indolo-quinolizidine derivatives of the general formula (I) or salts or optically active isomers thereof,

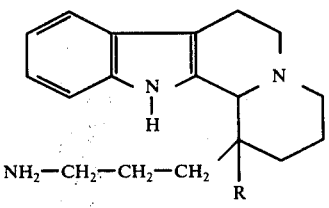

(I)

wherein R stands for an alkyl group, and pharmaceutical compositions containing the same, as well as to a process for the preparation thereof.

The new compounds according to the invention possess vasodilatating and hypotensive effects and can be used in the therapy as medicines. The new compounds according to the invention are completely devoid of harmful side-effects.

2 Claims, No Drawings

INDOLO (2,3-α)QUINOLIZINES

This invention relates to new indolo-quinolizidine derivatives and pharmaceutical compositions containing the same, as well as to a process for the preparation thereof.

More particularly, the invention relates to new indoloquinolizidine derivatives of the general formula (I) or salts or optically active isomers thereof

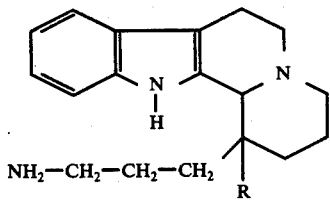

(I)

wherein R stands for an alkyl group.

Some of the 1,1-disubstituted indolo-quinolizidine compounds, such as vincamine and its derivatives, are known to possess valuable therapeutic effects. The preparation of these known indolo-quinolizidines was described by E. Wenkert et al. (J. Am. Chem. Soc. 87, 1580 /1956/), and by Szantay et al. (Tetrahedron Letters 1973, 191).

1,1-Disubstituted indolo-quinolizidines, containing an alkyl group and an aminoalkyl group in position 1 have, however, not been described so far.

In the compounds of the general formula (I) R represents a straight-chained or branched alkyl group, preferably a lower alkyl group with 1 to 6 carbon atoms. Of these groups e.g. the methyl, ethyl, n-propyl, isopropyl, n-butyl, isobutyl, tert-butyl, n-amyl, isoamyl and hexyl groups are to be mentioned. Particularly preferred are those compounds of the general formula (I) in which R stands for ethyl.

The new compounds of the general formula (I), or their salts or optically active isomers, respectively, are prepared according to the invention as follows:

a. a compound of the general formula (IV)

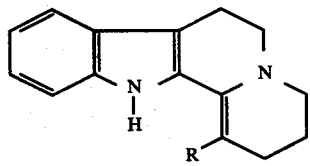

(IV)

wherein R stands for an alkyl group, or a salt thereof is reacted with acrylonitrile, the obtained compound of the general formula (III),

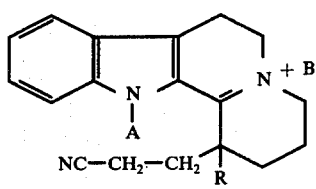

(III)

wherein R stands for alkyl, B stands for H₂O or an X⁻ anion derived from an acid, and if B is an X⁻ anion,
A represents hydrogen, whereas if B is H₂O, A represents an electron pair, is reduced partially, and the obtained compound of the general formula (II)

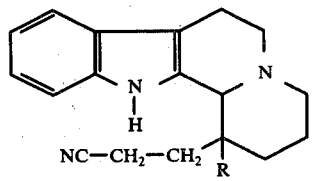

(II)

wherein R stands for alkyl, or a salt thereof is reduced; or b. a compound of the general formula (III), wherein R stands for alkyl, B stands for H₂O or an X⁻ anion derived from an acid, and if B is an X⁻ anion, A represents hydrogen, whereas if B is H₂O, A represents an electron pair, is reduced partially, and the obtained compound of the general formula (II), wherein R stands for alkyl, or a salt thereof is reduced; or c. a compound of the general formula (II), wherein R stands for alkyl, or a salt thereof is reduced; or d. a compound of the general formula (IV), wherein R stands for alkyl, or a salt thereof is reacted with acrylonitrile, and the obtained compound of the general formula (III), wherein R stands for alkyl, B stands for H₂O or an X⁻ anion derived from an acid, and if B is an X⁻ anion, A represents hydrogen, whereas if B is H₂O, A represents an electron pair, is reduced; or e. a compound of the general formula (III), wherein R stands for alkyl, B stands for H₂O or an X⁻ anion derived from an acid, and if B is an X⁻ anion, A represents hydrogen, whereas if B is H₂O, A represents an electron pair, is reduced, and, if desired, a racemic compound of the general formula (I), wherein R stands for alkyl, or a salt thereof is resolved, or an optically active compound of the general formula (I), wherein R stands for alkyl, or a salt thereof is subjected to racemization, and, if desired, a racemic or optically active compound of the general formula (I), wherein R stands for alkyl, is converted into its salt, or a salt of a racemic or optically active compound of the general formula (I), wherein R stands for alkyl, is converted into the free base.

The compounds of the general formulae (II) and (III), formed in the synthesis of the process according to the invention, are new substances. These compounds and the preparation thereof are also embraced by the scope claimed.

A method for the preparation of the starting substances of the general formula (IV) is described by E. Wenkert et al. (J. Am. Chem. Soc. 87, 1580 /1965/). According to this method, malonester is converted into diethyl ethyl-γ-bromopropylmalonate, this compound is hydrolysed and decarboxylated by heating it with hydrogen bromide, the obtained substance is esterified with diazomethane, the produced methyl 2-ethyl-5-bromo-valerate is condensed with tryptamine, and the resulting 1-(3-indolyl-ethyl)-3-ethyl-piperidone-2 is treated with phosphorous trichloride. If desired, the obtained salt is converted into the free base. According to another process, the starting substances of the general formula (IV) are prepared by reacting an α-alkyl-γ-hydroxypentanoyl-tryptamide with phosphorous oxychloride, and converting the resulting salt into the free base, if desired.

The compounds of the general formula (IV) are used, in accordance with the invention, preferably in the form of their salts. Particularly preferred are the respective acid addition salts, such as the perhalogenates (e.g. the perchlorates, perbromates, etc.). These acid addition salts are converted into the free bases prior to their reaction with acrylonitrile, preferably in the reaction mixture itself, by contacting them with a base. This is accomplished preferably with a dilute aqueous solution of an inorganic base, such as an alkali metal hydroxide (e.g. sodium hydroxide, potassium hydroxide, etc.). The base can be used optionally in an excess of 20 to 40% with respect to the theoretical amount. The bases having the general formula (IV) are liberated preferably in an inert, water-immiscible organic solvent, such as in a halogenated hydrocarbon (e.g. chloroform, carbon tetrachloride, dichloromethane, 1,2-dichloroethane, trichloroethylene, etc.). The liberation of the base is performed preferably in an inert gas atmosphere, particularly in nitrogen or argon atmosphere. Owing to the presence of a heterogeneous system, the reaction mixture is preferably stirred during the entire procedure. The base liberates after a short period of stirring, generally within 5 to 20 minutes. The temperature of this reaction may vary within wide limits, it is preferred, however, to conduct the reaction at room temperature. After liberation, the organic phase is separated and dried.

Acrylonitrile is added to the dried organic phase obtained in the above step. It is preferred to use an excess of acrylonitrile. The molar ratio of acrylonitrile and the starting compound having the general formula (IV) may vary e.g. between 2:1 and 8:1. The molar ratio is preferably about 5:1. The reaction temperature and time are not critical, it is preferred, however, to conduct the reaction at room temperature. When the mixture is allowed to stand at room temperature, the reaction time is generally 1 to 4 days. It is preferred to use freshly distilled acrylonitrile in the above step.

The obtained reaction mixture can be processed by usual methods, e.g. by evaporating the solvent in vacuo.

When the above process yields a compound of the general formula (IIIb),

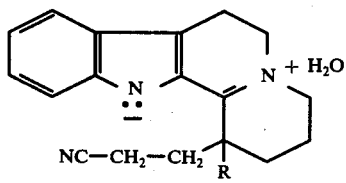

(IIIb)

wherein R stands for alkyl, it can be converted, if desired, into its acid addition salt of the general formula (IIIa),

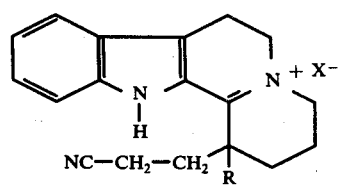

(IIIa)

wherein R and X⁻ each have the same meanings as defined above. For this purpose e.g. mineral acids, such as hydrogen halides (e.g. hydrochloric acid, hydrobromic acid, etc.), phosphoric acid, etc., organic carboxylic acids, such as acetic acid, propionic acid, glycolic acid, maleic acid, succinic acid, tartaric acid, citric acid, salicylic acid, benzoic acid, etc., alkylsulfonic acids, such as methanesulfonic acid, or arylsulfonic acids, such as p-toluenesulfonic acid, etc. can be applied.

The salt-formation is performed preferably in an inert solvent, particularly in an aliphatic alcohol, such as methanol. The starting base of the general formula (IIIb) is dissolved in the appropriate solvent, and the acid is added to this solution until a slightly acidic pH (about 6) is attained. Thereafter the precipitated compound of the general formula (IIIa) is separated from the reaction mixture.

The acid addition salts of the general formula (IIIa) can be converted, if desired, into the free bases having the general formula (IIIb) by contacting them with a base. For this purpose preferably an aqueous solution of an inorganic base, such as an alkali metal hydroxide (e.g. sodium hydroxide) is used. According to a preferred method, a salt of the general formula (IIIa) is suspended in water, then an inert organic solvent, such as a halogenated hydrocarbon (e.g. dichloromethane) is added to the suspension, and the obtained mixture is treated with a base under constant stirring and cooling, in an inert gas atmosphere. The base separates mostly in oily form, and is concentrated in the organic phase. According to our investigations, the structure of the resulting base corresponds to the general formula (IIIc),

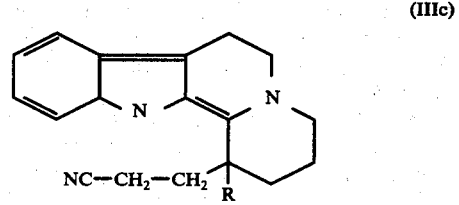

(IIIc)

wherein R has the same meaning as defined above. The obtained oily substance can be crystallized easily e.g. from an aliphatic alcohol, such as methanol, to obtain a crystalline substance having the general formula (IIIb).

The compounds of the general formula (III) contain as asymmetric carbon atom. The process described above yeilds the compounds of the general formula (III) in racemic form. The racemates can be resolved, if desired, by methods known per se, e.g. by forming diastereomeric salt pairs. The optically active compounds of the general formula (III) and their preparation are also embraced by the scope claimed.

If desired, the compounds of the general formula (III) can be subjected to further purification steps, such as recrystallization. As recrystallization solvent e.g. aliphatic alcohols (such as methanol or ethanol), ketones (such as acetone), aliphatic esters, particularly alkyl alkanecarboxylates (such as ethyl acetate), acetonitrile, or a mixture of such solvents (e.g. a mixture of ethyl acetate and ether) can be used. It is, however, not absolutely necessary to recrystallize the compounds of the general formula (III) prior to the next step of the process according to the invention, since crude compounds of the general formula (III) can also be used in the next reduction step.

In the next step of the process according to the invention the compounds having the general formula (III) are subjected to partial or complete reduction.

To perform the partial reduction, any reducing agent capable of saturating the endocyclic double bond without hydrogenating simultaneously the cyano group can be used. The reduction is performed preferably with a chemical reducing agent or by catalytic hydrogenation.

In chemical reduction, preferably a complex metal hydride, particularly a borohydride, such as lithium or sodium borohydride, or formic acid is used as reducing agent.

Of the complex metal hydrides the borohydrides are particularly preferred, because of their outstanding selectivity. When a borohydride is used as reducing agent, the reaction is performed in a solvent or suspending agent which is inert towards the reaction. One may use to advantage an aliphatic alcohol, such as methanol, or an aqueous alcohol, such as aqueous methanol.

The borohydride is added to the reaction mixture in excess, preferably in an amount of 3 to 10 moles, particularly about 6 moles per one mole of the starting substance. The reaction time and temperature are not critical, and their optimum values depend primarily on the reactivity of the starting substance used. The reaction is performed generally at about 0° C, by stirring the reaction mixture for about 30 minutes to about 3 hours.

According to a preferred method of the invention a compound of the general formula (IIIa) or (IIIb), wherein R and $X^-$ each have the same meanings as defined above, is suspended in an inert solvent, preferably in an aliphatic alcohol, the suspension is cooled to about 0° C, and the borohydride (preferably sodium borohydride) is added to the suspension in small portions at the same temperature.

The reaction mixture can be processed by methods known per se, e.g. by acidifying and concentrating the reaction mixture, dissolving the residue in water, rendering the solution alkaline, extracting the alkaline mixture, and evaporating the extract to dryness.

As mentioned above, formic acid can also be used as chemical reducing agent. Formic acid is added to the reaction mixture preferably as a substantially pure chemical (purity grade: 98 to 100 %) in excess, preferably in an amount of 2 to 4 moles, particularly about 3 moles per one mole of the starting substance. The excess of formic acid also serves as a solvent medium for the reaction. The reaction is performed at elevated temperatures, preferably at bath temperatures of 80° to 120° C, particularly at bath tempertures of 95° to 100° C. The reaction time usually ranges from 10 to 30 hours. It is preferable to heat the mixture for about 20 hours. the reaction is performed preferably under an inert gas, such as nitrogen or argon. the reaction mixture is processed in a known way, e.g. by diluting it with water, rendering the mixture alkaline, extracting the aqueous-alkaline solution, and separating the product from the extract.

If catalytically activated hydrogen is used as reducing agent, preferably a metal belonging to the subgroups of the Periodic System, such as palladium, platinum, nickel, iron, copper, cobalt, chromium, zinc, molybdenum, tungsten, etc. or an oxide or sulfide thereof is used as hydrogenating catalyst.

The catalysts to be used in the process of the invention can be prepared e.g. by reducing their stable oxides with hydrogen directly in the reaction vessel. This method can be used e.g. when finely divided platinum or palladium is to be applied as hydrogenating catalyst. Alternately, catalysts prepared by acidic or alkaline leaching of one metal from a binary alloy, such as Raney-nickel, can be used as well. The catalytic hydrogenation can also be performed in the presence of a supported catalyst; this enables to decrease considerably the amount of the expensive noble metals necessary for the reduction. Of the supports e.g. carbon (particularly charcoal), silica, alumina, and the sulfates and carbonates of alkaline earth metals are to be mentioned.

When the reduction is performed with catalytically activated hydrogen, one employs preferably palladium (particularly palladium-on-charcoal) or Raney-nickel as catalyst. The catalysts are always selected in accordance with the reaction conditions and the characteristics of the substance to be hydrogenated.

The catalytic reduction is performed in a solvent inert towards the reaction, such as water, alcohols, ethyl acetate, glacial acetic acid, etc., or mixtures of such solvents. The aliphatic alcohols, such as methanol, etc. proved to be the most preferred solvents. If platinum oxide is used as catalyst, the reaction is performed preferably in a neutral or slightly acidic medium, whereas if Raney-nickel is applied, the reaction is conducted preferably in a neutral or alkaline medium.

The temperature, pressure and time of the catalytic reduction may vary within wide limits depending on the starting substances. It is preferable, however, to conduct the reaction at room temperature and under atmospheric pressure until the cessation of the hydrogen uptake. The hydrogen uptake ceases generally within 10 minutes to 5 hours.

The reaction mixture is processed in a manner known per se, e.g. by filtering the mixture and evaporating the filtrate to dryness.

The catalytic hydrogenation is performed preferably as follows: a catalyst (preferably palladium-on-charcoal) is washed with a mixture of water and the solvent used in the hydrogenation process (preferably methanol), and the washed catalyst is prehydrogenated. Thereafter a solution of the appropriate starting substance of the general formula (IIIa) or (IIIb) in the above solvent is added to the pre-treated catalyst, and the resulting mixture is hydrogenated, preferably at room temperature and under atmospheric pressure, until the hydrogen uptake ceases.

The product is generally separated from the reaction mixture as a crystalline solid. If, however, an amorphous powder or an oily substance is obtained, it can usually be crystallized very easily from a suitable solvent, such as an aliphatic alcohol, e.g. methanol, etc.

The free bases of the general formula (II) obtained in the partial reduction step can be converted into their acid addition salts. For this purpose preferably pharmaceutically acceptable mineral or organic acids, such as hydrogen halides (e.g. hydrochloric acid, hydrobromic acid, etc.), phosphoric acid, organic carboxylic acids (e.g. acetic acid, propionic acid, glycolic acid, maleic acid, succinic acid, tartaric acid, citric acid, salicylic acid, benzoic acid, etc.), alkysulfonic acids (e.g. methanesulfonic acid), arysulfonic acids (e.g. p-toluenesulfonic acid) etc. can be used. In turn, the acid addition salts can be treated with a base to yield the compounds of the general formula (II) in the form of the free bases.

The salt formation is performed preferably in an inert solvent, particularly in an aliphatic alcohol, such as methanol. The base of the general formula (II) is dissolved in the solvent, and the mixture is acidified slightly (to about pH = 6) with the appropriate acid. The acid is added preferably in small portions. Thereafter the separated salt of the starting base is isolated from the reaction mixture.

The compounds of the general formula (II) contain an asymmetric carbon atom, they may exist therefore in the form of optically active isomers. The synthesis according to the invention yields racemic compounds of the general formula (II), which can be resolved into the individual optically active isomers by known methods.

The octahydro-indolo-quinolizines of the general formula (II) can be reduced further with any reducing agent capable of converting a cyano group into a primary amino group. The reduction is performed preferably with a chemical reducing agent in the presence of a hydrogenation catalyst.

The applicable catalysts are the same as listed in connection with the catalytic hydrogenation of the compounds having the general formula (III). Of these catalysts the nickel-containing substances, particularly Raney-nickel are the most preferred. The reduction is carried out in neutral media, or, more peferably, in slightly alkaline media, in order to avoid undesired side-reactions.

As chemical reducing agents, the complex metal hydrides mentioned in connection with the reduction of compounds having the general formula (III) can be applied. Of these complex metal hydrides the borohydrides, particularly sodium borohydride, have proved to be the most advantageous.

The reduction is carried out in a solvent or suspending agent inert towards the reaction, such as water, an aliphatic alcohol (e.g. methanol), or in a mixture thereof. The temperature of the reduction is not critical, it is performed generally between 30° C and the boiling point of the mixture. The reaction time depends on the starting substance, the reducing agent and the temperature, and varies generally between 1 and 10 hours.

The reduction is performed preferably as follows: A compound of the general formula (II) is dissolved in the appropriate solvent, the hydrogenation catalyst is added to the solution, and then the chemical reducing agent is introduced at a slightly elevated temperature. It is added preferably as a suspension formed with a dilute aqueous alkali. The reaction mixture is boiled for a little time, and thereafter, in order to ensure complete reduction, additional amounts of catalyst and reducing agent are added, and boiling is continued.

The reaction mixture is processed in a manner known per se, e.g. by filtering the mixture and evaporating the filtrate to dryness. When the end-product is obtained in oily form, it can be crystallized easily from an appropriate solvent.

One may also subject a compound of the general formula (III) directly to complete reduction. In this event a compound of the general formula (III) is reduced with a chemical reducing agent, preferably with a borohydride (such as sodium borohydride), in the presence of a hydrogenation catalyst as discussed above. Upon the action of this reducing system the hexahydro-indolo-quinolizine ring converts into the octahydro derivative, and the cyano group converts simultaneously into primary amino group. This reduction is performed in a manner described in connection with the reduction of the compounds having the general formula (II), only the amounts of the catalysts are different.

The reaction mixture can be processed as described above.

The compounds of the general formulae (III) and (II), formed as intermediates in accordance with the process of the invention, can be separated and purified before the next reaction step, one may, however, also conduct the next reaction step directly in the obtained reaction medium, without isolating the intermediate.

If desired, the compounds of the general formula (I) can be converted into their pharmaceutically acceptable acid addition salts. As salt-forming agent e.g. mineral acids, such as hydrogen halides (e.g. hydrochloric acid, hydrobromic acid, etc.) or phosphorous acid, organic carboxylic acids, e.g. acetic acid, propionic acid, glycolic acid, maleic acid, succinic acid, tartaric acid, citric acid, salicylic acid, benzoic acid, etc., alkylsulfonic acids, such as methanesulfonic acid, etc., or arylsulfonic acids, such as p-toluene-sulfonic acid, etc. can be used. In turn, the acid addition salts can be treated with a base to yield the compounds of the general formula (I) in the form of the free bases.

The salt formation is performed preferably in an inert solvent, particularly in an aliphatic alcohol, such as methanol. The base of the general formula (I) is dissolved in the solvent, and the mixture is acidified slightly (to about pH =6) with the appropriate acid. The acid is added preferably in small portions. Thereafter the resulting salt is precipitated from the reaction mixture preferably by adding a water-immiscible organic solvent, such as diethyl ether.

If desired, the obtained compounds of the general formula (I) or their salts can be subjected to further purification steps, e.g. recrystallization.

The recrystallization is performed preferably in a mixture of an aliphatic alcohol, such as methanol, and an ether-type organic solvent, such as diethyl ether.

The compounds of the general formula (I) and their salts contain an asymmetric carbon atom, hence they may exist in the form of optically active isomers. The racemates can be resolved into the individual optically active isomers. The racemates can be resolved into the individual optically active isomers by methods known per se.

The process of the invention enables to produce the compounds of the general formula (I) with high yields and in forms easy to identify. The analytical data of the obtained compounds are in good agreement with the calculated values. The structures of the obtained products can be confirmed further by IR and NMR spectroscopy.

The compounds of the general formula (I) and their pharmaceutically acceptable acid addition salts possess valuable biological properties. According to the results of the tests carried out on narcotized dogs, the compounds possess significant vasodilatating effects. The compounds increase primarily the blood flow of the limbs, or they may cause a significant and durable drop in blood pressure.

The tests were performed on dogs narcotized with chloralose-urethane. The blood flow of the limbs was measured at the arteria femoralis, whereas the cerebral blood flow was investigated by measuring the flow of the arteria carotis interna. The circulation resistance was calculated from the blood pressure and blood flow values.

The compounds under examination were administered in intravenous dosages of 1 mg./kg. The observed changes were expressed as percentages in relation to the controls. 6 animals were used in each of the tests, and the data of Table 1 are the mean values calculated for these groups.

For comparison purposes the respective data of apovincaminic acid ethyl ester, the most active one of the compounds with related structures (see Hungarian Pat. No. 163,434) are also given.

Table 1

| Substance | (1) | (2) | (3) | (4) | (5) | (6) |
|---|---|---|---|---|---|---|
| (A) | +58 | −35 | +16 | −20 | −28 | +14 |
| (B) | +301.5 | −60.3 | +1.1 | −5.3 | −22.6 | +6.3 |

Notes:
(1) blood flow of the limbs
(2) circulation resistance of the limb blood vessels
(3) cerebral blood flow
(4) circulation resistance of the cerebral blood vessels
(5) blood pressure
(6) heart rate
(A) apovincaminic acid ethyl ester (reference substance)
(B) a compound of the general formula (I), wherein R is ethyl As appears from the date of the Table, the new compounds, according to the invention are about 5 times as active as the reference substance with respect to the increase of the blood flow in the limbs, whereas their activities exceed about 1.5 to 2 times that of the reference substance with respect to the decrease of blood pressure.

The effective intravenous or oral dosage of the new compounds may vary within about 0.1 to 2 mg./kg. body weight. It should be noted, however, that the actual dosage is always determined in accordance with the needs of the patient, thus in some instances dosages lower or high than those mentioned above are to be applied.

The compounds of the general formula (I) or the pharmaceutically acceptable acid addition salts thereof can be converted into pharmaceutical compositions suitable for enteral or parenteral administration. These compositions may contain the new compounds according to the invention either along or in combination with other biologically active substances. When preparing the pharmaceutical compositions the active agent(s) is(are) admixed with conventional inert, non-toxic, pharmaceutically acceptable carriers and/or diluents. As carrier e.g. water, gelatine, lactose, starch, magnesium stearate, talc, vegetable oils, gum arabic, polyalkylene glycols, vaseline, etc. can be used. The amount of the solid carrier may vary within wide limits; the dosage units may contain e.g. 25 to 1000 mg. of solid carrier. The compositions may optionally contain conentional pharmaceutical auxiliary agents, such as preservatives, salts for adjusting the osmotic pressure, buffers, flavouring agents, etc. The pharmaceutical compositions can be prepared in conventional forms, e.g. as solid formulations (tablets, coated tablets, capsules, etc.) or as liquid preparations (e.g. solutions, suspensions, emulsions, etc.). The obtained compositions can be sterilized, or subjected to other finishing operations, if necessary.

The invention is elucidated in detail by the aid of the following non-limiting Examples.

EXAMPLE 1

1-Ethyl-1-(3-aminopropyl)-1,2,3,4,6,7,12,12b-octahydroindolo (2,3-a)quinolizine 2.0 g. (6.20 mmoles) of (1-ethyl-1,2,3,4,6,7-hexahydro-indolo[2,3-a]quinolizin-1-yl)-propionitrile are dissolved in 100 ml. of methanol, and 2 g. of Raney-nickel, thoroughly pre-washed with water and methanol, are added. The reaction mixture is warmed to 48° to 50° C under stirring, and a suspension of 2.0 g. (53 mmoles) of sodium borohydride in 8 ml. of 8 n sodium hydroxide is added. At the beginning of the reaction a vigorous bubbling can be observed. The reaction mixture is stirred for 30 minutes, thereafter it is refluxed for 3 hours. The mixture is cooled to about 50° C, and 2 g. of Raney-nickel, pre-treated as described above, and a suspension of 2.0 g. (53 mmoles) of sodium borohydride in 8 ml. of 8 n sodium hydroxide are added. When the bubbling ceases the reaction mixture is heated to boiling and refluxed for 3 hours. Thereafter the reaction mixture is cooled, the catalyst is filtered off, and washed with methanol. The filtrate is evaporated in vacuo. The oily residue is dissolved in a minimum amount of methanol, and the solution is acidified slightly by adding methanol saturated with anhydrous hydrochloric acid. The methanol solution is diluted with ether, and the precipitated hydrochloride is filtered off. The obtained salt, weighing 2.20 g., is recrystallized from a mixture of methanol and ether to obtain 1.85 g. (77.8%) of 1-ethyl-1-(3-aminopropyl)-1,2,3,4,6,7,12,12b-octahydro-indolo(2,3-a)quinolizine dihydrochloride; m.p.: 248–251° C.

Analysis:
Calculated for $C_{20}H_{29}N_3.2HCl$ (M = 384.38): C: 62.48%, H: 8.12%, N: 10.93%,
Found: C: 62.22%, H: 7.80%, N: 10.71%.
IR-spectrum (in KBr): 3305–3410 cm$^{-1}$ (ind.—NH).

EXAMPLE 2

1-Ethyl-1-(3-aminopropyl)-1,2,3,4,6,7,12,12b-octahydro-indole(2,3-a)quinolizine 3.10 g. (10.1 mmoles) of 1-ethyl-(2-cyanoethyl)-1,2,3,4,6,7,12,12b-octahydro-indolo(2,3-a)quinolizine are dissolved in 250 ml. of methanol, the solution is heated to 48° to 50° C, and 2 g. of Raney-nickel, pre-washed with distilled water and methanol, are added. Thereafter a mixture of 0.50 g. (16.3 mmoles) of sodium borohydride and 2 ml. of 8 n sodium hydroxide is added to the suspension. Bubbling sets in immediately, which lasts about 30 minutes after the addition of the last portion of the borohydride. Thereafter additional 2 g. of Raney-nickel, pre-treated as described above, and a suspension of 0.50 g. (16.3 mmoles) of sodium borohydride in 2 ml. of 8 n sodium hydroxide are added. When the bubbling ceases the reaction mixture is heated to boiling and refluxed for 3 hours. After the termination of the reaction the catalyst is filtered off, washed with methanol, and the filtrate and wash are evaporated in vacuo. The obtained crude, oily substance is processed as described in Example 1 to obtain 3.20 g. (83.5%) of 1-ethyl-1-(3-aminopropyl)-1,2,3,4,6,7,12,12b-octahydroindolo(2,3-a)quinolizine. The white, crystalline substance melts at 249–251° C, and is identical with the product prepared according to Example 1.

EXAMPLE 3

(1-Ethyl-1,2,3,4,6,7-hexahydro-indolo[2,3-a]quinolizin-1-yl)-propionitrile (betaine structure)

10.0 g. (28.5 mmoles) of 1-ethyl-2,3,4,6,7,12-hexahydro-indolo(2,3-a)quinolizinium perchlorate are dissolved in 100 ml. of dichloromethane, and 75 ml. of distilled water and 20 ml. of 2 n sodium hydroxide are added to the solution under constant stirring in argon atmosphere. The reaction mixture is stirred for 10 minutes, thereafter the organic phase is separated and dried over anhydrous potassium carbonate. The drying agent is filtered off, 10 ml. (142 mmoles) of freshly distilled acrylonitrile are added to the filtrate, the mixture is flushed with argon, and allowed to stand at room temperature for 2 days, during which period the solution darkens considerably. Thereafter the solution is evaporated in vacuo under argon atmosphere (bath temperature: maximum 40° to 50° C). The residual dark red oil is triturated with 5 ml. of methanol, and the formed orange-red crystals are filtered off. The thus-obtained crude product, weighing 8.10 g., is recrystallized from 15-fold volume of methanol. 7.30 g. (79.4%) of crystalline (1-ethyl-1,2,3,4,6,7-hexahydro-indolo[2,3-a]quinolizin-1-yl)-propionitrile are obtained; m.p.: 122–123° C.

Analysis:
  calculated for $C_{20}H_{23}N_3$ (M = 323.42): C: 74.27%, H: 7.79%, N: 12.99%,
  found: C: 74.05%, H: 7.87%, N: 12.92%.

IR-spectrum (KBr): 2280 cm$^{-1}$ (—CN), 1662 and 1608 cm$^{-1}$ (=C=N$^{30}$=).

UV-spectrum (in methanol): $\lambda_{max}$: 242 nm (log $\epsilon$ = 4.0026), 254 nm (log $\epsilon$ = 3.9777), 362 nm (log $\epsilon$ = 4.3944).

EXAMPLE 4

1-Ethyl-1-(2-cyanoethyl)-1,2,3,4,6,7-hexaydro-12H-indolo[2,3-a]quinolizinium perchlorate 1 g. of (1-ethyl-1,2,3,4,6,7-hexahydro-indolo[2,3-a]quinolizin-1-yl)-propionitrile are dissolved in 20 ml. of hot methanol, and the solution is acidified to pH = 6 with 70% perchloric acid. The separated yellow crystals are filtered off and dried to obtain 1.05 g. of 1-ethyl-1-(2-cyanoethyl)-1,2,3,4,6,7-hexaydro-12H-indolo[2,3-a]quinolizinium perchlorate; m.p.: 209–211° C. After recrystallization from methanol, the product melts at 211–212° C.

Analysis:
  calculated for $C_{20}H_{24}N_3ClO_4$ (M = 405.86): C: 59.18%, H: 5.96%, N: 10.35%,
  found: C: 59.23%, H: 6.02%, N: 10.49%.

IR-spectrum (in KBr): 3290 cm$^{-1}$ (ind.—NH), 2360 cm$^{-1}$ (—CN), 1620 cm$^{-1}$ (=C=N$^+$=).

EXAMPLE 5

1-n-Butyl-1-(2-cyanoethyl)-1,2,3,4,6,7-hexahydro-12H-indolo(2,3-a)quinolizinium perchlorate 5.0 g. (13.3 mmoles) of 1-n-butyl-2,3,4,6,7,12-hexahydro-indolo(2,3-a)quinolizinium perchlorate are suspended in 50 ml. of dichloromethane, and 50 ml. of distilled water and 10 ml. of 2 n sodium hydroxide are added to the suspension under constant stirring in argon atmosphere. The reaction mixture is stirred for 10 minutes, thereafter the organic phase is separated, and dried over anhydrous potassium carbonate. The drying agent is filtered off, 5.0 ml. (71 mmoles) of freshly distilled acrylonitrile are added to the filtrate, the mixture is flushed with argon, and allowed to stand at room temperature for 3 days. Thereafter the reaction mixture is evaporated in vacuo, the red oily residue is dissolved in 5 ml. of methanol, and the solution is acidified to pH = 6 with 70% perchloric acid. The crystallization of the product is initiated by scraping the wall of the flask. The flask is put into refrigerator. The separated yellow crystals are filtered off, washed with cold methanol, and the obtained 4.20 g. of product (m.p.: 215–220° C) are recrystallized from 5-fold volume of methanol. 3.70 g. (64.1%) of 1-n-butyl-1-(2-cyanoethyl)-1,2,3,4,6,7-hexahydro-12H-indolo(2,3-a)quinolizinium perchlorate are obtained in the form of yellow needles; m.p.: 224–226° C.

Analysis:
  calculated for $C_{22}H_{28}N_3ClO_4$ (M = 433.91): C: 60.87%, H: 6.50%, N: 9.68%,
  found: C: 60.60%, H: 6.29%, N: 9.82%.

IR-spectrum (in KBr): 3328 cm$^{-1}$ (ind.—NH), 2304 cm$^{-1}$ (—CN), 1625 and 1650 cm$^{-1}$ (=C=N$^+$=).

EXAMPLE 6

1-n-Butyl-1,2,3,4,6,7-hexahydro-12H-indolo(2,3-a)-quinolizine perchlorate (starting substance)

42.65 g. (135 mmoles) of α-n-butyl-δ-hydroxypentanoyl-tryptamide are dissolved in 250 ml. of freshly distilled phosphoryl chloride, and the solution is refluxed for 8 hours. Thereafter the solution is evaporated in vacuo, and the obtained dark brown oily residue is dissolved in 300 ml. of dichloromethane. 300 ml. of distilled water are added to the solution, and the mixture is rendered alkaline (pH =14) with 40% sodium hydroxide solution under ice cooling. The mixture is shaken well, and the organic phase is separated. The aqueous phase is extracted with 2×100 ml. of dichloromethane. The organic solutions are combined, dried over magnesium sulfate, and the solvent is evaporated in vacuo. The red oily residue is dissolved in a minimum amount of methanol, and the solution is acidified to pH = 6 with 70% aqueous perchloric acid. A yellow, crystalline substance starts immediately to separate. The mixture is cooled in a refrigerator, and the crystals are filtered off. The obtained 29.90 g. (61.7%) of crude product (m.p.: 198–200° C) is recrystallized from methanol. The purified product melts at 201–202° C.

Analysis:
  calculated for $C_{19}H_{25}N_2ClO_4$ (M = 380.86): C: 59.91%, H: 6.61%, N: 7.35%,
  found: C: 60.26%, H: 6.67%, N: 7.03%.

IR-spectrum (in KBr): 3240 cm$^{-1}$ (ind.—NH), 1629 cm$^{-1}$ (=C=N$^+$=).

UV-spectrum (in methanol): $\lambda_{max}$ = 359 nm (log $\epsilon$ = 4.3598).

EXAMPLE 7

1-Ethyl-1,2,3,4,6,7-hexahydro-indolo[2,3-a]quinolizin-1-yl)-propionitrile (betaine structure)

40 ml. of dichloromethane are added to a suspension of 1.00 g. of 1-ethyl-1-(2-cyanoethyl)-1,2,3,4,6,7-hexahydro-12H-indolo(2,3-a)quinolizinium perchlorate in 100 ml. of distilled water, and the pH of the mixture is adjusted to 10 to 11 with 40% sodium hydroxide solution. During this operation the mixture is cooled with water and stirred in argon atmosphere. After some minutes of stirring the separated red organic phase is removed, and the aqueous phase is extracted with 20 ml. of dichloromethane. The organic solutions are combined, dried over magnesium sulfate, and the solvent is evaporated in vacuo. The obtained 0.75 g. of red, oily residue is triturated with 1 ml. of methanol, and the resulting orange-red crystals are filtered off. 0.72 g. of (1-ethyl-1,2,3,4,6,7-hexahydro-indolo[2,3-a]quinolizin-1-yl)-propionitrile are obtained; m.p.: 122–123° C.

EXAMPLE 8

1α-Ethyl-1β-(2-cyanoethyl)-1,2,3,4,6,7,12,12bβ-octahydro-indolo(2,3-a)quinolizine a. 1 g. of 5% palladium-on-carbon catalyst is washed well with distilled water and methanol, and the catalyst is pre-hydrogenated in a small amount of methanol. When the hydrogen uptake ceases a solution of 1.50 g. (4.64 mmoles) of (1-ethyl-1,2,3,4,6,7-hexahydro-12H-indolo[2,3-a]quinolizin-1-yl)-propionitrile in 150 ml. of methanol is added, and the mixture is hydrogenated at room temperature under atmospheric pressure. The mixture takes up the calculated amount (110 ml.) of hydrogen within 15 minutes. When the hydrogen uptake ceases the catalyst is filtered off, washed with methanol, and the filtrate and wash are evaporated in vacuo. The obtained solid, weighing 1.35 g., is recrystallized from 20-fold volume of methanol to obtain 1.20 g. (84.8 %) of 1α-ethyl-1β-(2-cyanoethyl)-1,2,3,4,6,7,12,12bβ-octahydro-indolo[2,3-a]quinolizine. The crystalline substance melts at 228°–229° C.

Analysis:

calculated for $C_{20}H_{25}N_3$ (M = 307.42): C: 78.13%, H: 8.20%, N: 13.67%, found: C: 78.36%, H: 8.39%, N: 13.38%.

IR-spectrum (in KBr): 3370 cm$^{-1}$ (ind.-NH), 2248 cm$^{-1}$ (—CN).

NMR-spectrum (in deuterochloroform): $\tau$ = 2.09 (1H, ind.—NH), 2.38–2.91 (4H, aromatic protons), 6.58 (1H at the anellation point), 9.13 (3H, —CH$_3$).

b. A suspension of 1.50 g. (4.64 mmoles) of (1-ethyl-1,2,3,4,6,7-hexahydro-12H-indolo[2,3-a]quinolizin-1-yl)propionitrile in 100 ml. of methanol is cooled to 0° C, and 1.0 g. (26.5 mmoles) of sodium borohydride are added to the suspension in small portions at the same temperature, under constant stirring. After the addition the reaction mixture is stirred for 1 hour, then it is acidified to pH = 3 with 5 n hydrochloric acid. The acidic mixture is concentrated in vacuo to a final volume of 10 ml. The resulting suspension is admixed with distilled water, and the pH of the obtained mixture is adjusted to 10 to 11 with 40% aqueous sodium hydroxide solution under cooling. The alkaline mixture is extracted with three portions (20 ml., 10 ml. and 10 ml., respectively) of dichloroethane. The organic solutions are combined, dried over magnesium sulfate, and evaporated in vacuo. The obtained solid residue is recrystallized from methanol to obtain 1.20 g. (84.8%) of a crystalline powder melting at 228°–229° C. This product is identical with the compound obtained according to step a) above.

c. 12.0 g. (37.2 mmoles) of (1-ethyl-1,2,3,4,6,7-hexahydro-indolo[2,3-a]quinolizin-1-yl)-propionitrile are dissolved in 4.75 ml. (5.78 g., 125 mmoles) of formic acid (purity grade: 98 to 100%), and the mixture is heated on a steam bath (bath temperature: 95 to 100° C) under argon atmosphere for 20 hours. Thereafter the acidic solution is diluted with 50 ml. of distilled water, and the pH of the mixture is adjusted to 10 to 11 with 40% aqueous sodium hydroxide solution. During this operation the mixture is cooled. The aqueous solution is extracted with three portions (50 ml., 30 ml. and 20 ml., respectively) of dichloroethane. The organic solutions are combined, dried over magnesium sulfate, and evaporated in vacuo. The solid residue is recrystallized from methanol to obtain 9.05 g. (79.2 %) of crystalline 1α-ethyl-1β-(2-cyanoethyl)-1,2,3,4,6,7,12,12bβ-octahydro-indolo(2,3-a)quinolizine, m.p.: 227°–229° C. This compound is identical with the product prepared in step a) above.

EXAMPLE 9

1α-n-Butyl-1β-(2-cyanoethyl)-1,2,3,4,6,7,12,12bβ-octahydro-indolo(2,3-a)quinolizine a. 0.8 g. of an 5% palladium-on-carbon catalyst is washed with distilled water and methanol, and then it is prehydrogenated in about 20 ml. of methanol. When the hydrogen uptake ceases, a solution of 0.75 g. (1.73 mmoles) of 1-n-butyl-1-(2-cyanoethyl)-1,2,3,4,6,7-hexahydro-12H-indolo-(2,3-a)quinolizinium perchlorate in 600 ml. of methanol is added, and the mixture is hydrogenated at room temperature under atmospheric pressure. The mixture takes up the calculated amount of hydrogen within about 2 hours, thereafter the hydrogen uptake ceases. The catalyst is filtered off, the filtrate is evaporated in vacuo, and the obtained salt is crystallized from 2 ml. of methanol. 6.60 g. (79.6 %) of 1α-n-butyl-1β-(2-cyanoethyl)-1,2,3,4,6,7,12,12bβ-octahydroindolo(2,3-a) quinolizinium perchlorate are obtained; m.p.: 227°–229° C under decomposition.

b. A suspension of 2.15 g. (5.97 mmoles) of 1-n-butyl-1-(2-cyanoethyl)-1,2,3,4,6,7-hexahydro-12H-indolo(2,3-a)-quinolizinium perchlorate in 750 ml. of methanol is cooled to 0° C, and 1.50 g. (39.7 mmoles) of sodium borohydride are added in small portions to the suspension at the same temperature. After the introduction of the reducing agent the mixture is stirred for additional 1 hour, then it is acidified to pH = 3 with 5 n aqueous hydrochloric acid. The mixture is evaporated in vacuo to a final volume of 10 ml., the obtained concentrate is diluted with 200 ml. of distilled water, and the pH of the mixture is adjusted to 10 to 11 with 40% aqueous sodium hydroxide solution under ice cooling. The aqueous solution is extracted with three portions (50 ml., 30 ml. and 20 ml., respectively) of dichloroethane. The organic solutions are combined, dried over magnesium sulfate, and evaporated in vacuo. The oily residue is crystallized from twofold volume of ethanol. 0.95 g. (57.1%) of 1α-n-butyl-1β-(2-cyanoethyl)-1,2,3,4,6,7,12,12bβ-octahydro-indolo-(2,3-a)quinolizine are obtained. The white, crystalline substance melts at 188°–189° C.

Analysis:

calculated for $C_{22}H_{29}N_3$ (M = 335.48): C: 78.76%, H: 8.71%, N: 12.53%, found: C: 78.98%, H: 8.72%, N: 12.34%.

IR-spectrum (in KBr): 3395 cm$^{-1}$ (ind. -NH), 2310 cm$^{-1}$ (—CN).

NMR-spectrum (in deuterochloroform): $\tau$ = 1.97 (1H, ind.—NH), 2.42–2.98 (4H, aromatic protons), 9.12 (3H, —CH$_3$).

What we claim is:

1. A compound of the formula (I),

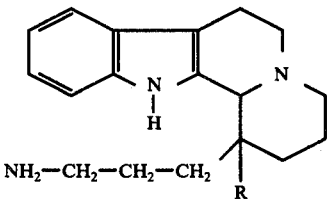

(I)

wherein R stands for alkyl, having from 1 to 6 carbon atoms, or a pharmaceutically acceptable salt thereof or optically active isomer thereof.

2. 1-Ethyl-1-(3-aminopropyl)-1,2,3,4,6,7,12,12b-octahydro-indolo(2,3-a)quinolizine.